United States Patent
Weiss et al.

(10) Patent No.: US 11,318,280 B2
(45) Date of Patent: May 3, 2022

(54) CATHETER BEING USABLE IN A MAGNETIC RESONANCE IMAGING SYSTEM

(75) Inventors: Steffen Weiss, Hamburg (DE); Oliver Lips, Hamburg (DE); Sascha Krueger, Hamburg (DE); David Bernd, Huettblek (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2611 days.

(21) Appl. No.: 13/142,426

(22) PCT Filed: Jan. 11, 2010

(86) PCT No.: PCT/IB2010/050082
§ 371 (c)(1),
(2), (4) Date: Jan. 3, 2012

(87) PCT Pub. No.: WO2010/082150
PCT Pub. Date: Jul. 22, 2010

(65) Prior Publication Data
US 2012/0101362 A1  Apr. 26, 2012

(30) Foreign Application Priority Data
Jan. 15, 2009 (EP) .................................. 09150594

(51) Int. Cl.
*A61M 25/00* (2006.01)
*G01R 33/28* (2006.01)
(Continued)

(52) U.S. Cl.
CPC ..... *A61M 25/0021* (2013.01); *A61B 18/1492* (2013.01); *A61M 25/0082* (2013.01);
(Continued)

(58) Field of Classification Search
CPC ...... A61M 2025/0166; A61M 25/0021; A61M 25/0082; A61M 25/10; G01R 33/287
(Continued)

(56) References Cited

U.S. PATENT DOCUMENTS 5,431,168 A * 7/1995 Webster, Jr. ....... A61B 18/1492
600/435
6,061,587 A  5/2000 Kucharczyk et al.
(Continued)

FOREIGN PATENT DOCUMENTS

WO WO2006010908 2/2006
WO WO2006113267 10/2006

OTHER PUBLICATIONS

Wikipedia contributors. Electromagnetic coil. Wikipedia, The Free Encyclopedia. Nov. 15, 2015, 12:23 UTC. Available at: https://en.wikipedia.org/w/index.php?title=Electromagnetic_coil&oldid=690749705. Accessed Jan. 19, 2016.*
(Continued)

*Primary Examiner* — Katherine L Fernandez
(74) *Attorney, Agent, or Firm* — Sherry Austin

(57) ABSTRACT

The present invention relates to a catheter (2) for applying energy to an object (6) and a magnetic resonance imaging system (1) for localizing the catheter (2). The catheter (2) comprises an energy application element for applying energy to the object (6), and a cavity for providing a magnetic resonance fluid from which magnetic resonance signals generated by the magnetic resonance imaging system (1) are receivable, wherein the cavity is adapted for providing a cooling fluid as the magnetic resonance fluid for cooling the energy application element. The catheter (2) comprises further a tracking coil (15) for tracking the catheter (2), wherein the tracking coil (15) is adapted to receive the magnetic resonance signals from the magnetic resonance fluid. Thus, the magnetic resonance fluid fulfils at
(Continued)

least two functions, providing magnetic resonance signals for tracking the catheter (2) and cooling the energy application element.

6 Claims, 5 Drawing Sheets

(51) Int. Cl.
*A61B 18/14* (2006.01)
*A61M 25/01* (2006.01)
*A61M 25/10* (2013.01)
*A61B 18/00* (2006.01)
*A61B 34/20* (2016.01)

(52) U.S. Cl.
CPC .. *G01R 33/287* (2013.01); *A61B 2018/00023* (2013.01); *A61B 2018/00029* (2013.01); *A61B 2018/00744* (2013.01); *A61B 2034/2051* (2016.02); *A61M 25/10* (2013.01); *A61M 2025/0166* (2013.01)

(58) Field of Classification Search
USPC ........ 600/411, 420, 423, 424, 431, 434, 435
See application file for complete search history.

(56) References Cited

U.S. PATENT DOCUMENTS

| 6,272,370 | B1* | 8/2001 | Gillies | A61M 25/0105 |
|---|---|---|---|---|
| | | | | 324/309 |
| 6,575,969 | B1 | 6/2003 | Rittman, III et al. | |
| 7,205,768 | B2 | 4/2007 | Schulz et al. | |
| 2002/0103430 | A1 | 8/2002 | Hastings et al. | |
| 2003/0055449 | A1 | 3/2003 | Lee et al. | |
| 2003/0195412 | A1* | 10/2003 | Gillies et al. | 600/411 |
| 2004/0193039 | A1 | 9/2004 | Weber | |
| 2008/0091193 | A1 | 4/2008 | Kauphusman et al. | |
| 2008/0275395 | A1 | 11/2008 | Asbury et al. | |
| 2009/0054803 | A1* | 2/2009 | Saadat | A61B 1/0008 |
| | | | | 600/546 |
| 2009/0171188 | A1* | 7/2009 | Paul | A61B 18/1492 |
| | | | | 600/422 |
| 2010/0072994 | A1* | 3/2010 | Lee | G01N 24/08 |
| | | | | 324/307 |
| 2010/0152731 | A1* | 6/2010 | de la Rama et al. | 606/41 |

OTHER PUBLICATIONS

S. Weiss et al., "Transmission Line for Improved RF Safety of Interventional Devices", Magnetic Resonance in medicine 54:182-189 (2005).
W.R. Nitz et al., "On the Heating of Linear conductive Structures as Guide Wires and Catheters in Interventional MRI", Journal of Magnetic Resonance Imaging 13:105-114 (2001).
C.L. Dumoulin et al., "Real-Time Position Monitoring of Invasive Devices using Magnetic Resonance", MRM 29:411-415(1993).
J.L. Ackerman et al., "Rapid 3D Tracking of Small RF Coils", Dept. of Radiology, Massachusetts General Hospital and Harvard Medical School, Boston, MA 02114, pp. 1131-1132.
Wikipedia: Inductor. http://en.wikipedia.org/wiki/lnductor#Air-core_inductor.
Sullivan, C.R. et al., "Design and Fabricationof Low-Loww Toroidal Air-Core Inductors". IEEE Power Electronics Specialists Conference, Jun. 2007, pp. 1754-1759.
"An introduction to the air cored coil". http://info.ee.surrey.ac.uk/Workshop/advice/coils/air_coils.html.

* cited by examiner

CATHETER BEING USABLE IN A MAGNETIC RESONANCE IMAGING SYSTEM

FIELD OF THE INVENTION

The present invention relates to a catheter for applying energy to an object being usable in a magnetic resonance imaging system, a magnetic resonance fluid that is usable within the catheter and a magnetic resonance imaging system being usable with the catheter. The invention relates further to a method for applying energy to an object, a method for manufacturing the catheter and a computer program for applying energy to an object.

BACKGROUND OF THE INVENTION

An ablation catheter is known, which is usable in electrophysiological operations monitored by a magnetic resonance imaging system. The ablation catheter comprises an external tracking coil arranged at the outside of the distal tip of the catheter. The tracking coil receives magnetic resonance signals, which are used for determining the position of the tip of the catheter. This determination of the position of the tip of the catheter based on magnetic resonance signals received by the tracking coil often lacks reliability because of a weak magnetic resonance signal.

SUMMARY OF THE INVENTION

It is an object of the present invention to provide a catheter for applying energy to an object which can be localized more reliably by using a magnetic resonance imaging system. It is a further object of the present invention to provide a magnetic resonance imaging system which can localize the catheter more reliably and to provide a corresponding method and computer program for applying energy to an object. It is a further object of the present invention to provide a method for manufacturing the catheter.

In an aspect of the present invention a catheter for applying energy to an object being usable in a magnetic resonance imaging system is provided, wherein the catheter comprises:

an energy application element for applying energy to an object, a cavity for providing a magnetic resonance fluid from which magnetic resonance signals are receivable, wherein the cavity is adapted for providing a cooling fluid for cooling the energy application element as the magnetic resonance fluid, a tracking coil for tracking the catheter, the tracking coil being adapted for receiving the magnetic resonance signals from the magnetic resonance fluid.

Since the catheter comprises the cavity for providing a magnetic resonance fluid from which magnetic resonance signals are receivable and since the catheter comprises the tracking coil for tracking the catheter, wherein the tracking coil is adapted for receiving the magnetic resonance signals from the magnetic resonance fluid, the cavity itself can comprise the magnetic resonance fluid, wherein this magnetic resonance fluid allows to produce a magnetic resonance signal, even if outside the catheter a magnetic resonance fluid is not present. Furthermore, the magnetic resonance fluid can be adapted to generate a magnetic resonance signal with a desired strength. Thus, a magnetic resonance fluid can be used being adapted such that the strength of the magnetic resonance signals and, thus, the reliability of localization of the catheter in a magnetic resonance imaging system which is based on the strength of the magnetic resonance signal is optimized. This allows improving the reliability of localizing a catheter within a magnetic resonance imaging system. Furthermore, the magnetic resonance fluid does not only have the function of generating the magnetic resonance signal, but also cools the energy application element of the catheter, i.e. it is not necessary to have several cavities for several kinds of fluid. It is, for example, not necessary to have a first cavity for providing a cooling fluid and a second cavity for providing the magnetic resonance fluid. This allows reducing the space needed for providing the different functions.

The magnetic resonance fluid is a fluid that generates magnetic resonance signals in a magnetic resonance imaging system. The magnetic resonance fluid is preferentially a liquid, further preferred water.

The catheter can comprise one or several tracking coils.

The tracking coil is preferentially an active magnetic resonance receive coil for determining its own position within a magnetic resonance imaging system.

It is further preferred that the cavity is located within the most sensitive region of the tracking coil. This further increases the strength of the signal of the tracking coil which is used for localizing the catheter within a magnetic resonance imaging system, thereby further increasing the reliability of localizing the catheter within the magnetic resonance imaging system.

It is further preferred that the cavity is located within the tracking coil. Since the region within the tracking coil is a region of high magnetic resonance sensitivity, by locating the cavity and, thus, the magnetic resonance fluid within the tracking coil, the strength of the signal of the tracking coil used for localizing the catheter within the magnetic resonance imaging system is further increased. This further improves the reliability of localizing the catheter in a magnetic resonance imaging system.

It is further preferred that the cavity is widened at a location at which the tracking coil surrounds the cavity. Since the cavity is widened at a location at which the tracking coil surrounds the cavity, more magnetic resonance fluid can be provided within the tracking coil thereby further increasing the strength of the signal generated by the tracking coil, which is used for localizing the catheter within a magnetic resonance imaging system. This further improves the reliability of localizing the catheter in a magnetic resonance imaging system.

It is further preferred that the tracking coil is arranged such that it does not add to the outer catheter profile. Preferentially, the tracking coil is arranged inside the catheter. Since the tracking coil does not add to the outer catheter profile, the catheter can easily be introduced into an object like a heart of a human being or of an animal.

It is further preferred that the cavity and the tracking coil are located at a distal end of the catheter.

The cavity is preferentially a fluid channel for allowing the magnetic resonance fluid flowing within the catheter, in particular, for guiding the magnetic resonance fluid to the tracking coil. This allows guiding fresh spins of the magnetic resonance fluid to the tracking coil which further increases the strength of the signal generated by the tracking coil, which is used for localizing the catheter in a magnetic resonance imaging system. This further increases the reliability of localizing the catheter in a magnetic resonance imaging system. The fluid channel can be a lumen of the catheter, or a tube which is preferentially located within the lumen of the catheter.

The energy application element is preferentially an ablation element for ablating an object like a heart, in particular, heart tissue of a heart wall. Such a catheter comprising an ablation element can be regarded as an ablation catheter, wherein the position of this ablation catheter can be determined within a magnetic resonance imaging system. This allows determining the position at which energy is applied, in particular, at which an ablation is performed. The catheter comprising the cavity for providing a magnetic resonance fluid, the tracking coil and the energy application element is preferentially used for electrophysiological operations, in particular, at a heart of a patient. Preferentially, the energy application element, the tracking coil and the cavity are located at the tip of the catheter.

The energy application element is preferentially an electrode for applying electrical energy or an optical element for applying light energy or a cryo element for cryo ablation or an ultrasound transducer for ultrasound ablation.

Preferentially, at least a part of the cavity is arranged within the energy application element for guiding the magnetic resonance fluid through the energy application element for cooling the energy application element. For example, the energy application element can comprise a feed-through forming a first part of the cavity and a cooling tube can be provided as a second part of the cavity, wherein the cooling tube is connected to the feed-through for allowing the magnetic resonance fluid to flow through the energy application element for cooling the energy application element.

It is further preferred that the cavity is adapted to allow the magnetic resonance fluid leaving the catheter, wherein the tracking coil is adapted to excite magnetization in the magnetic resonance fluid such that the magnetic resonance visibility of the magnetic resonance fluid is increased. The magnetic resonance fluid can leave the catheter for irrigation. Furthermore, the tracking coil can excite, saturate or prepare the magnetization of the magnetic resonance fluid by means of "transmission" of radio frequency (RF) using the tracking coil. For this purpose, a RF pulse can be provided to a connection cable of the catheter and transmitted by the tracking coil. Preferably, a wide bandwidth RF pulse is used to be able to excite magnetization irrespective of any selection gradients used for imaging. Due to the local sensitivity of the tracking coil magnetic resonance fluid is selectively excited which can thus be selectively followed by magnetic resonance imaging, in particular, in real time. In one embodiment, only the tracking coil and not a body RF coil of a magnetic resonance imaging system is used for spin excitation during magnetic resonance (MR) imaging, which results in an image where only the magnetic resonance fluid exiting the catheter is visible with positive contrast visualizing the flow of the magnetic resonance fluid around the catheter tip and its further path. Combined, e.g. interleaved with conventional anatomic imaging where the body RF coil is used for spin excitation, the spatial relation of the magnetic resonance fluid and the tissue and the catheter can be visualized. Alternatively to selective excitation and imaging of the magnetic resonance fluid, the magnetic resonance fluid can be saturated to visualize the magnetic resonance fluid as signal void during imaging. Alternatively, RF pulses for magnetization preparation as inversion pulses may be applied with the tracking coil. These concepts can be used to visualize and measure flow of the magnetic resonance fluid. This may also be used to visualize and verify proper catheter contact and catheter cooling efficiency, in particular, proper catheter tip contact and catheter tip cooling efficiency.

The catheter is preferentially connectable to a catheter position determination unit for determining the position of the catheter based on the magnetic resonance signal received by the tracking coil.

In a further aspect of the present invention a magnetic resonance fluid from which magnetic resonance signals are receivable is provided, wherein the magnetic resonance fluid is a cooling fluid for cooling an energy application element of a catheter for applying energy to an object and is adapted to be provided by a cavity of the catheter and to allow generating magnetic resonance signals being detectable by a tracking coil of the catheter, wherein the magnetic resonance fluid comprises a magnetic resonance contrast agent. This further increases the signal generated by the tracking coil and, thus, further increases the reliability of localizing the catheter within a magnetic resonance imaging system.

Furthermore, if the magnetic resonance fluid is guided through a channel of the catheter to the distal end of the catheter, in particular, by means of a cooling tube, a portion of the catheter like the distal end that may be deflectable or the full length of the catheter may be visualized in magnetic resonance images due to the presence of the magnetic contrast agent. Moreover, if the magnetic resonance fluid can leave the catheter, for example, for irrigation purposes, the magnetic resonance fluid comprising the magnetic resonance contrast agent can be used for marking ablation sites by doping them with contrast agent. For example, the magnetic resonance fluid may enter the ablated tissue more easily due to the tissue being ablated. Thus, ablated tissue can be marked in comparison to non-ablated tissue, if an ablation procedure is applied to tissue of, for example, a wall of the heart.

In a further aspect of the present invention a magnetic resonance imaging system for localizing a catheter is provided, wherein the catheter comprises an energy application element for applying energy to an object, a cavity for providing a cooling fluid for cooling the energy application element as a magnetic resonance fluid from which magnetic resonance signals are receivable and a tracking coil for tracking the catheter, the tracking coil being adapted for receiving the magnetic resonance signals from the magnetic resonance fluid, wherein the magnetic resonance imaging system is adapted to generate a magnetic resonance signal in a magnetic resonance fluid present in the cavity of the catheter such that the generated magnetic resonance signal is receivable by the tracking coil, wherein the magnetic resonance imaging system comprises a catheter position determination unit for determining the position of the catheter based on the magnetic resonance signal received by the tracking coil.

In a further aspect of the present invention a method for applying energy to an object by using a catheter as defined in claim 1 and a magnetic resonance imaging system as defined in claim 9 is provided, wherein the method comprises following steps:

applying energy to the object by the energy application element of the catheter, providing a cooling fluid for cooling the energy application element as magnetic resonance fluid in the cavity of the catheter, generating a magnetic resonance signal in the magnetic resonance fluid present in the cavity of the catheter such that the generated magnetic resonance signal is receivable by the tracking coil, receiving the generated magnetic resonance signal by the tracking coil, determining the position of the catheter based on the received magnetic resonance signal by the catheter position determination unit.

It should be noted that the step of applying energy to the object can be performed before, during or after the cooling fluid is provided and the position of the catheter is determined.

In a further aspect of the present invention a method for manufacturing a catheter as defined in claim 1 is provided, wherein the method comprises the steps of:

a) providing a catheter,
b) providing the catheter with an energy application element for applying energy to an object,
c) providing the catheter with a cavity for providing a cooling fluid for cooling the energy application element being a magnetic resonance fluid from which magnetic resonance signals are receivable,
d) providing the catheter with a tracking coil for tracking the catheter, the tracking coil being adapted for receiving the magnetic resonance signals from the magnetic resonance fluid.

It is further preferred that steps c) and d) comprise following steps:
arranging the tracking coil around the cavity,
arranging the cavity with the tracking coil within the catheter. Preferentially the tracking coil is arranged around the cavity being preferentially a fluid channel. This allows pre-mounting the tracking coil around the cavity, which might be a cooling tube, thereby reducing the number of steps needed for manufacturing the catheter.

It is further preferred that after arranging the tracking coil around the cavity following steps are performed:
connecting the tracking coil with a tuning and matching network,
filling the cavity with the cooling fluid being the magnetic resonance fluid,
adapting the tuning and matching network for the tracking coil,
connecting the tuning and matching network to a connection element for connecting the tuning and matching network with a magnetic resonance receiver. The connection element is preferentially a connection cable. The tuning and matching network preferentially comprises capacitances, wherein the capacitances of the tuning and matching network are adapted for the tracking coil. For example, the tuning and matching network is adapted such that the reflection of a signal applied to the proximal end of the tuning and matching network is minimized. This can be achieved by adapting the tuning and matching network such that the scatter parameter S11 is minimized.

The tracking coil is preferentially tuned and matched to the connection cable like any conventional MR receive coil for optimal signal reception. This is preferentially achieved by the tuning and matching network comprising capacitors. The tuning and matching network is preferentially a miniature tuning and matching network. The simplest network consists of one capacitor in series and one capacitor in parallel to the tracking coil. The capacitances must be adapted for tuning and matching of the tracking coil and depend sensitively on the impedance of the coil. Since the tracking coils can only be manufactured with some tolerances in impedance which also is influenced by the coil loading (the presence of magnetic resonance fluid, for example, water, in the cavity), the capacitances are adapted for the tracking coil in the loaded condition. For external coils this means that they must be immersed in water during adaptation of the capacitances, which can only be done after sealing the coil while access to the capacitances must still be provided, which is very hard to achieve in practice. Contrarily, an internal tracking coil can be prepared on the cavity filled with magnetic resonance fluid, i.e. in the loaded condition, the capacitances on the network can be adapted, the connection cable can be connected, and this subassembly can be inserted into the catheter. This separate preparation of the tracking subsystem simplifies catheter manufacturing considerably.

In a further aspect of the present invention, a computer program for applying energy to an object by using a catheter as defined in claim 1 and a magnetic resonance imaging system as defined in claim 9 is provided, wherein the computer program comprises program code means for causing the catheter and the magnetic resonance imaging system to carry out the steps of the method as defined in claim 10, when the computer program is run on a computer controlling the catheter and the magnetic resonance imaging system.

It shall be understood that the catheter of claim 1, the magnetic resonance fluid of claim 8, the magnetic resonance imaging system of claim 9, the method for applying energy to an object of claim 10, the method for manufacturing a catheter of claim 11 and the computer program of claim 14 have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
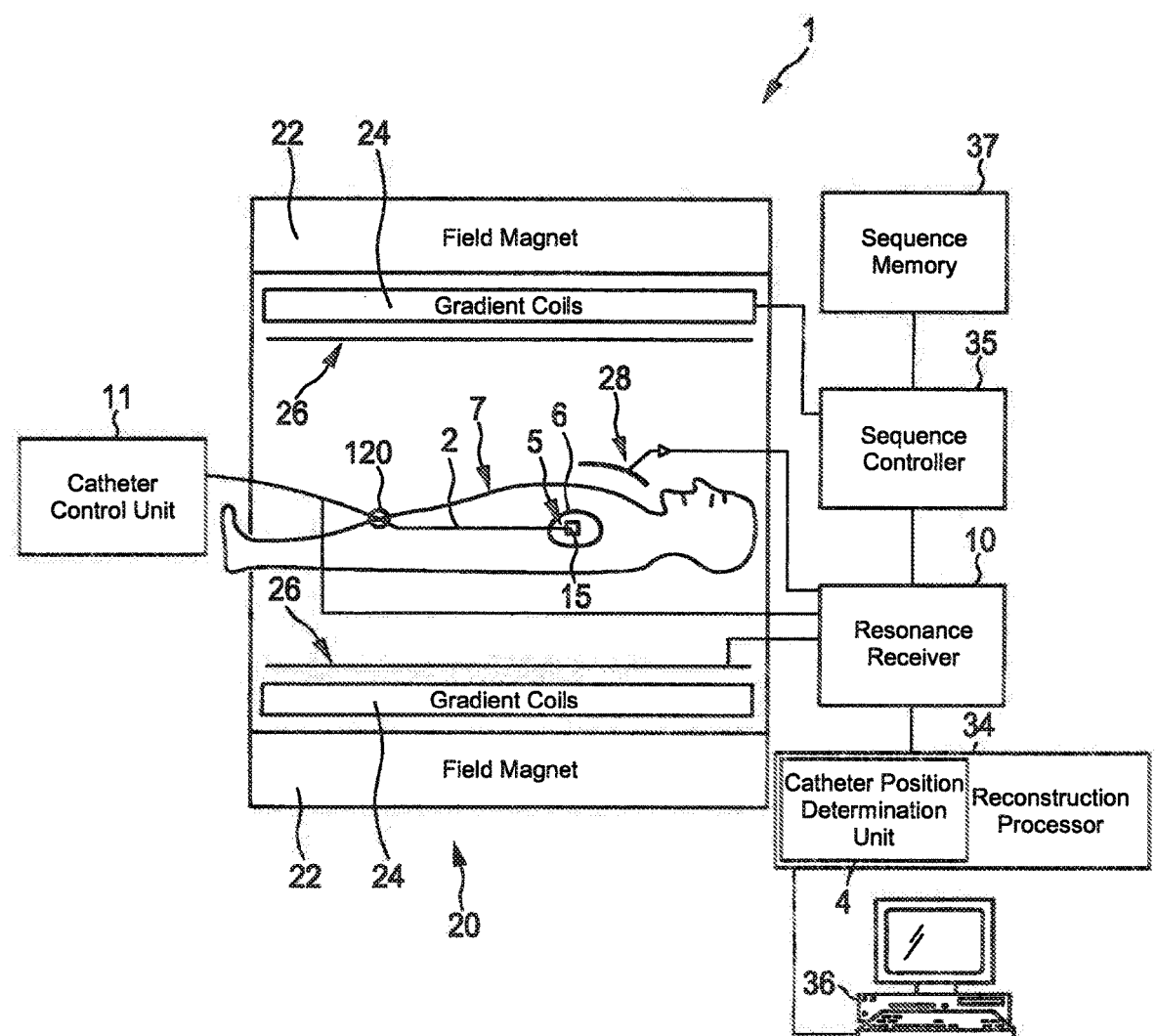
FIG. 1 shows schematically and exemplarily a magnetic resonance imaging system.

FIG. 1 shows schematically and exemplarily a magnetic resonance imaging system 1 for localizing a catheter 2. A distal end 5 of the catheter 2 has been steered into the heart 6 of a person 7 located in an imaging region of the magnetic resonance imaging system 1. The catheter 2 is connected to a catheter control unit 11. The catheter 2 enters the body of the person 7 at location 120 and comprises a tracking coil 15 at the distal end 5. The magnetic resonance imaging system 1 includes a main field magnet 22 for generating a B0 field in the imaging region. Gradient coils 24 induce a gradient magnetic field across the B0 field, typically along three orthogonal axes. A whole body RF coil 26 transmits RF pulses to excite and manipulate resonance in the person 7 in the imaging region. The whole body RF coil 26 optionally also receives RF resonance signals from the imaging region. A surface or other local RF coil 28, if present, receives the resonance signals. Optionally, the local coil can also induce and manipulate resonance. A sequence controller 35 controls the RF and gradient coils 24 to implement a selected magnetic resonance imaging sequence or a tracking sequence. A sequence memory 37 stores these sequences. A magnetic resonance receiver 10 receives the magnetic resonance signals from the tracking coil 15, the whole body RF coil 26 and the local RF coil 28, and a reconstruction processor 34 reconstructs the received resonance signals into an image representation or reconstructs tracking positions. A user interface 36 enables an operator to select imaging and tracking sequences to be performed, reconstruction operations, image formats and the like and displays reconstructed images and catheter positions.

The magnetic resonance receiver 10 is connected to the tracking coil 15 on the distal end 5 of the catheter 2 via a connection cable. The magnetic resonance signal received by the tracking coil 15 and forwarded to the magnetic resonance receiver 10 via the connection cable is input into a catheter position determination unit 4 for determining the position of the catheter 2, in particular, of the part of the catheter comprising the tracking coil 15, based on the magnetic resonance signal received by the tracking coil. The catheter position determination unit 4 is integrated in the reconstruction processor 34.

The catheter control unit 11 being in this embodiment an ablation unit comprises an energy source connected via a guiding element to an energy application element at the distal end 5 of the catheter 2. For example, the catheter control unit 11 comprises an electrical energy source for applying electrical energy or a light source for applying light energy. In addition or alternatively, the catheter control unit 11 can be adapted to allow a cryo element at the distal end 5 of the catheter 2 performing a cryo ablation. Moreover, the catheter control unit 11 can be adapted to control an ultrasound transducer at the distal end 5 of the catheter 2 for performing ultrasound ablation. Thus, the catheter control unit 11 is preferentially adapted to control an energy application element located at the distal end 5 of the catheter 2.

The energy application element is preferentially an ablation element for ablating an object like a heart, in particular, heart tissue of a heart wall. Such a catheter 2 comprising an ablation element can be regarded as an ablation catheter, wherein the position of this ablation catheter 2 can be determined with the magnetic resonance imaging system 1. This allows determining the position at which energy is applied, in particular, at which an ablation is performed. The catheter 2 comprising the cavity for providing a magnetic resonance fluid, the tracking coil and the energy application element is preferentially used for electrophysiological operations, in particular, at a heart of a person. The energy application element, the tracking coil and the cavity are located at the tip, i.e. the distal end 5, of the catheter 2.

The catheter 2 comprises, as it will be explained in more detail further below, a cavity for providing a cooling fluid for cooling the energy application element as a magnetic resonance fluid from which magnetic resonance signals are receivable. The magnetic resonance imaging system 1 is adapted to generate a magnetic resonance signal in a magnetic resonance fluid present in the cavity of the catheter 2 such that the generated magnetic resonance signal is receivable by the tracking coil. Thus, for localizing the catheter, in particular, the part of the catheter in which the tracking coil is located, the magnetic resonance imaging system 1 generates a magnetic resonance signal in the magnetic resonance fluid present in the cavity of the catheter 2 and the generated magnetic resonance signal is received by the tracking coil and forwarded to the catheter position determination unit 4 via the connection cable and the magnetic resonance receiver 10, wherein the catheter position determination unit 4 determines the position of the catheter based on the magnetic resonance signal received by the tracking coil.

Figure 2:
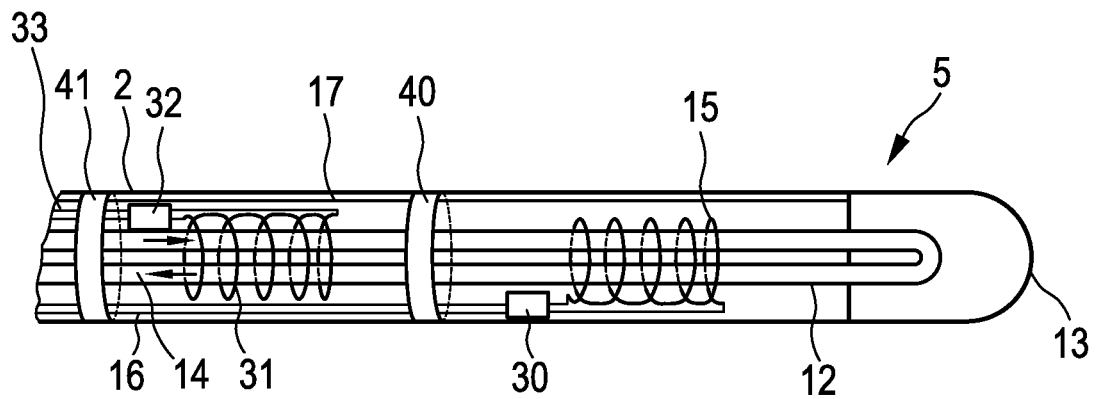
FIG. 2 shows schematically and exemplarily an embodiment of a catheter tip.

FIG. 2 shows schematically and exemplarily the distal end 5 of the catheter 2. The catheter 2 comprises a cavity 12 for providing a magnetic resonance fluid 14 from which magnetic resonance signals are receivable. The cavity 12 is adapted for providing a cooling fluid as the magnetic resonance fluid 14. In this embodiment, the cavity 12 is a fluid channel for guiding the magnetic resonance fluid through the tracking coil to the tip of the catheter and back towards the proximal end of the catheter. The fluid channel 12 is a cooling tube located in a lumen of the catheter 2. However, in another embodiment, the fluid channel can be manufactured in another way, for example, a lumen itself can form the fluid channel.

The tracking coil 15 of the catheter 2 is adapted for receiving a magnetic resonance signal generated in the magnetic resonance fluid 14 flowing through the fluid channel being the cavity 12.

The magnetic resonance fluid 14 is preferentially cooling water for cooling an ablation element 13 of the catheter. Thus, the magnetic resonance fluid 14 fulfils two functions, generating a magnetic resonance signal for being received by the tracking coil 15 and cooling the ablation element 13.

The cavity 14 is preferentially formed by a first part being a feed-through of the ablation element 13 and a second part being a fluid channel which is connected to the feed-through of the ablation element 13. This allows the magnetic resonance fluid to flow through the ablation element 13 for cooling the same. In another embodiment, the cavity can be formed by a fluid channel only, wherein the fluid channel is adapted to provide the magnetic resonance fluid to the ablation element and wherein the fluid channel is arranged within a feed-through of the ablation element for allowing the magnetic resonance fluid to flow through the ablation element for cooling the same.

The tracking coil 15 is an active magnetic resonance receive coil for determining its own position within the magnetic resonance imaging system 1. The tracking coil 15 is arranged at or near the tip of the catheter 2, or at other relevant parts of the catheter 2, for determining the position of the tip or of the other relevant parts. During ablation with the ablation element 13, it is desired to know its location as precisely as possible. Hence the tracking coil 15 is preferentially positioned as near as possible to the ablation element 13. A second tracking coil 31 (not shown in FIG. 1) is used arranged in a known distance from the ablation element 13 to be able to calculate the position of the ablation element 13 from the positions of the two tracking coils 15, 31. In particular, since the spatial relation between the two tracking coils 15, 31 and the ablation element 13 is known, the determined positions of the two tracking coils 15, 31 can be used by the catheter position determination unit 4 for determining the position of the ablation element. For example, a vector can be determined pointing from the position of the second tracking coil 31 to the position of the tracking coil 15, wherein the position of the ablation element 13 can be determined by adding this vector to a known vector between the ablation element 13 and the tracking coil 15. The tracking coils 15, 31 can be arranged as schematically shown in FIG. 2. In another embodiment, they can be arranged and dimensioned in another way. For example, the two tracking coils 15, 31 can only be displaced with respect to each other in the longitudinal direction, without a rotation with respect to each other as schematically shown in FIG. 2, or the two tracking coils can comprise different diameters and/or a different number of windings. Furthermore, also more than two tracking coils can be present.

In FIG. 2, the distal end 5 of the catheter 2 further comprises two recording or pacing elements 40, 41 being ring electrodes. These ring electrodes 40, 41 can be used for recording of an intracardiac electrogram or for bipolar pacing. During recording of an intracardiac electrogram and pacing it is desirable to know the position of the center between the electrode pair, which is the best estimate of the effective recording or pacing location. The tracking coil 31 is located at the center of such an electrode pair 40, 41 to directly measure this location. Preferentially, all tracking coils 15, 31 are located beside and not within any electrode to prevent shielding of the excitation signal transmitted by the whole body RF coil 26, and to prevent detuning of the tracking coils 15, 31 due to inductive coupling to the ring electrodes 40, 41.

Preferentially, projections of the entire person 7, or in general of the entire object to be imaged, onto one spatial direction are acquired with the tracking coils 15, 31 which can be regarded as miniature tracking coils. The tracking coils 15, 31 are connected to the magnetic resonance receiver 10 via connection elements 16, 33 being preferentially RF cables, in particular, miniature connection RF cables, and tuning and matching networks 30, 32. The connection elements 16, 33 and the tuning and matching networks 30, 32 are located within the catheter 2. After a non-selective excitation of magnetization in a large volume containing the catheter 2 by the whole body RF coil 26, the magnetization is read out during a read-out gradient in one spatial dimension, for example, the x-direction. This provides a projection of the signal onto the x-direction. The projection effectively contains only a signal peak at a specific location and noise elsewhere. The specific location corresponds to the x-coordinate of the respective tracking coil. Repeated for the y- and z-directions, the complete position of the tracking coils 15, 31 can be determined, in particular, within few ten milliseconds. A more detailed description of the determination of the position of the tracking coils within a magnetic resonance imaging system, in particular, of a real time position monitoring of invasive devices using magnetic resonance, was disclosed by Ackermann D. L. et al. in Proc. of 5th SMRM, 1131 (1986) and by C. L. Dumoulin et al. in "Real-time position monitoring of invasive devices using magnetic resonance", Magn. Reson. Med. 29, 411-415 (1993).

A problem in this respect is posed by the fact that the excitation RF field generated by a body RF coil system 26 of the magnetic resonance imaging system 1, may induce RF common mode currents in the electrical connection cables 16, 33 in the catheter 2; these currents may cause substantial heating or even burning of body tissue next to the tracking coil. This is explained for example by Nitz W R, Oppelt A, Renz W et al. in "On the heating of linear conductive structures as guide wires and catheters in interventional MRI", J Magn Reson Imaging 2001; 13:105-114. This RF heating problem has so far prevented the use of active tracking coils in patients.

DE 102 49 239 A1 discloses a way to suppress these hazards by means of several transformers introduced into the connection cable contained in the catheter. While achieving RF safety, these transformers on the other hand decrease the signal-to-noise ratio of the signal of the tracking coil ("Transmission Line for Improved RF Safety of Interventional Devices", Weiss S. et al., Magn Reson Med 2005; 54:182). If the signal-to-noise ratio is too low, the position of the peak in the tracking projections and thus the respective spatial coordinate cannot be determined unambiguously and position tracking becomes unreliable. In a clinical application it is thus mandatory to provide the highest possible signal-to-noise ratio with the tracking coils 15, 31 in the first place.

The catheter 2 comprises an ablation element 13 being an ablation electrode at the catheter tip. The ablation element 13 is connected to the catheter control unit 11 via an electrical, optical, or cryo connection, in particular, via a wire 17.

The most sensitive region of the tracking coils 15, 31 is within the tracking coil. The fluid channel 12 is therefore located within the tracking coils 15, 31.

The tracking coils 15, 31 are located within the catheter 2 such that the tracking coils do not add to the outer catheter profile.

The magnetic resonance fluid 14 is a cooling fluid for cooling the ablation element and comprises preferentially a magnetic resonance contrast agent. This increases the signal generated by the tracking coils 15, 31 and, thus, further increases the reliability of localizing the catheter 2 within the magnetic resonance imaging system 1. Furthermore, since the magnetic resonance fluid 14 is guided through the fluid channel 12 along a length of the catheter 2 to the distal end 5 of the catheter 2, this length of the catheter 2 may be visualized in magnetic resonance images due to the presence of the magnetic contrast agent. Moreover, if in an embodiment, the magnetic resonance fluid can leave the catheter, for example, for irrigation purposes, the magnetic resonance fluid comprising the magnetic resonance contrast agent can be used for marking ablation sites by doping them with the contrast agent. For example, the magnetic resonance fluid may enter the ablated tissue more easily due to the tissue being ablated. Thus, an ablated tissue can be marked in comparison to non-ablated tissue, if an ablation procedure is applied to the tissue of, for example, a wall of the heart.

Preferred as magnetic resonance fluids are the same fluids as used for cooled tip ablation catheters used in X-ray-guided interventions. These are generally saline solutions, and in case of open irrigation catheters physiological saline solutions. These saline solutions can be mixed with conventional MR contrast agents based on Gadolinium, e.g. Omniscan® or Magnevist®.

The catheter control unit 11 is preferentially adapted to control the flow of the magnetic resonance fluid 14 within the fluid channel 12 and to control the ablation element 13.

Figure 3:
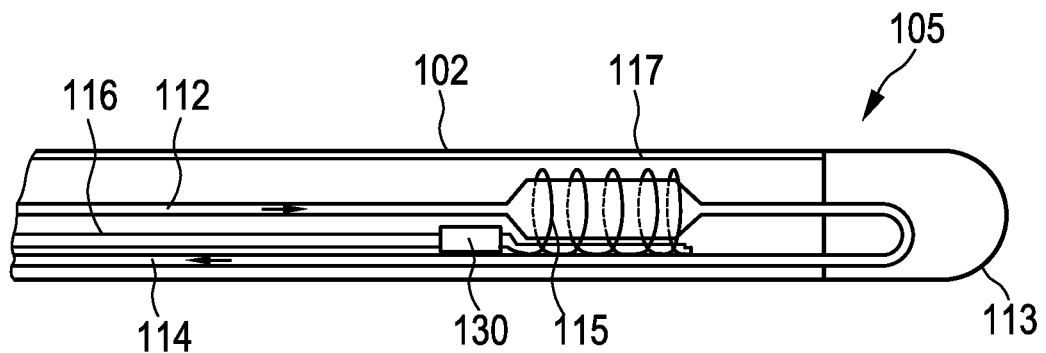
FIG. 3 shows schematically and exemplarily another embodiment of a catheter tip.

FIG. 3 shows schematically and exemplarily another embodiment of a distal end 105 of a catheter 102.

Also the distal end 105 of the catheter 102 shown in FIG. 3 comprises a tracking coil 115 surrounding a cavity 112 being a fluid channel for guiding magnetic resonance fluid, in particular, from the proximal end of the catheter, to the catheter tip and back towards the proximal end for cooling the catheter tip. An ablation element 113 is located at the catheter tip being controllable by the catheter control unit 11 via an electrical connection 117 being a wire in this embodiment. The tracking coil 115 is connectable to the magnetic resonance receiver 10 via a tuning and matching network 130 and electrical connection 116.

The distal ends of the catheters shown in FIGS. 2 and 3 differ from each other with respect to the arrangement of the tracking coil and the fluid channel. In FIG. 3, the fluid channel 112 is widened at a location at which the tracking coil 115 surrounds the fluid channel 112. Since the fluid channel 112 is widened at the location at which the tracking coil 115 surrounds the fluid channel 112, more magnetic resonance fluid 114 can be provided within the tracking coil 115 thereby increasing the strength of the signal generated by the tracking coil 115, which is used for localizing the catheter 102 within the magnetic resonance imaging system.

Figure 4:
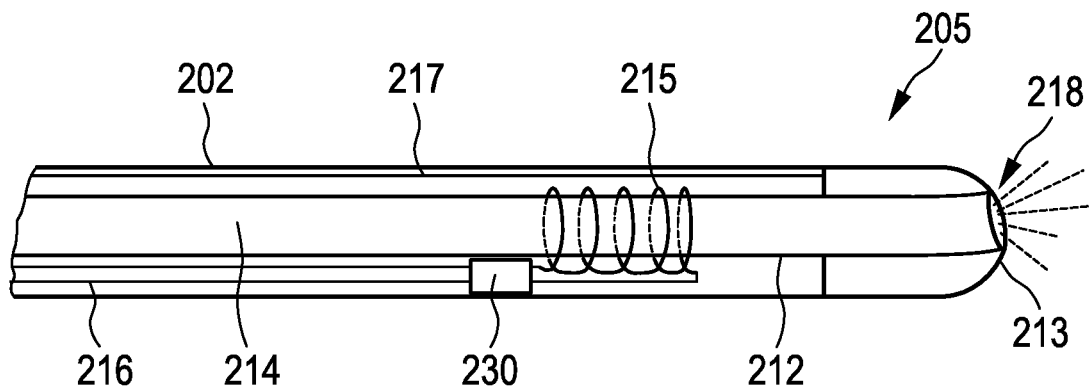
FIG. 4 shows schematically and exemplarily a further embodiment of a catheter tip.

FIG. 4 shows schematically and exemplarily a further embodiment of a distal end 205 of a catheter 202. The catheter 202 comprises a cavity being a fluid channel 212 being adapted to allow magnetic resonance fluid 214 leaving the catheter 202. The tracking coil 215 surrounds the fluid channel 212 and is adapted to excite magnetization in the magnetic resonance fluid such that the magnetic visibility of the magnetic resonance fluid 214 is increased. The magnetic resonance fluid 214, which cools an ablation electrode 213, can leave the catheter 202 for irrigation through an opening 218. Furthermore, the tracking coil 215 can excite, saturate or prepare the magnetization of the magnetic resonance fluid 214 by means of "transmission" of radio frequency using the tracking coil 215. For this purpose RF pulses can be provided to a connection cable 216 of the catheter 202 and transmitted by the tracking coil 215. Preferably, a wide bandwidth radio frequency pulse is used to be able to excite magnetization irrespective of any selection gradients used for imaging. Due to the local sensitivity of the tracking coil 215 the magnetic resonance fluid 214 is selectively excited which can thus be selectively followed by magnetic resonance imaging, in particular, in real time. Due to the selective excitation, any imaging process involving excitation of spins for imaging the patient in a wide field of view are thus only minimally disturbed. In an embodiment, only the tracking coil 215 and not a body radio frequency coil of the magnetic resonance imaging system is used for spin excitation during magnetic resonance imaging, which results in an image where only the magnetic resonance fluid 214 exiting the catheter 202 is visible with positive contrast visualizing the flow of the magnetic resonance fluid 214 around the catheter tip and its further path. Combined, for example, interleaved with conventional anatomic imaging where the body radio frequency coil is used for spin excitation, the spatial relation of the magnetic resonance fluid 214 and the tissue and the catheter 202 can be visualized. Alternatively to selective excitation and imaging of the magnetic resonance fluid 214, the magnetic resonance fluid 214 can be saturated to visualize the magnetic resonance fluid as signal void during imaging. As a further alternative, radio frequency pulses for magnetization preparation as inversion pulses may be applied with the tracking coil 215. These various concepts can be used to visualize and measure flow of the magnetic resonance fluid 214. This may also be used to visualize and verify proper catheter contact and catheter cooling efficiency, in particular, proper catheter tip contact and catheter tip cooling efficiency.

The distal end 205 of the catheter 202 shown in FIG. 4 comprises the electrode 213 as an ablation element which may be contacted with the catheter control unit 11 and the tracking coil 215 is connectable with the magnetic resonance receiver 10 via the tuning and matching network 230 and the electrical connection 216.

FIGS. 2 to 4 display a short solenoidal coil as embodiment of the tracking coil 15, 115, 215, 315 and the second tracking coil 31 which is preferential for a precise measurement of the position of the respective point of the catheter. During catheter manipulation, e.g. in catheter with deflectable tips, it may be desirable to visualize the curve of the entire tip section of the catheter. In one embodiment this may be accomplished by an elongated receive coil 335, e.g. a elongated single loop coil either connected to a separate tuning and matching network and connection element 16, or connected in series with one of the short solenoidal tracking coils as schematically and exemplarily displayed in FIG. 5. The curve of the entire tip section of the catheter is visualized by acquiring magnetic resonance images with the magnetic resonance system 1 using the elongated receive coil 335 as a receive coil, such that these images contain only signal at the curve of the catheter. In the same imaging process, other receive coils as local RF coils 28 or the whole body RF coil 26 can be used for acquisition of magnetic resonance images, such that these images contain anatomic information in the same field of view.

Figure 5:
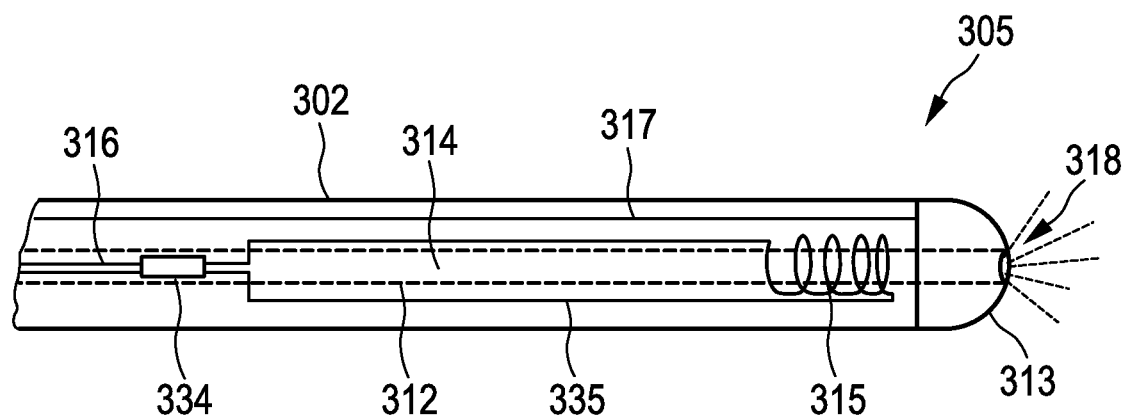
FIG. 5 shows schematically and exemplarily a further embodiment of a catheter tip.

The distal end 305 of the catheter 302 shown in FIG. 5 comprises a fluid channel 312 indicated by broken lines. The fluid channel 312 is located within the two tracking coils 315, 335 and comprises magnetic resonance fluid 314 being a cooling fluid for cooling an ablation element 313. This means, the two tracking coils 315, 335 surround the fluid channel 312, i.e. in the case of the tracking coil 335 the fluid channel 312 is preferentially located between the two longitudinal portions of the tracking coil 335. Through an opening 318 at the tip of the catheter 302 the magnetic resonance fluid can leave the catheter for irrigation. An ablation element 313 is located at the catheter tip. The ablation element 313 is connectable to the catheter control unit 11 via an electrical, optical, or cryo connection, in particular, via a wire 317. The two tracking coils 315, 335 are connected to a tuning and matching network 334 which is connectable to the magnetic resonance receiver 10 via an electrical connection 316.

Figure 6:
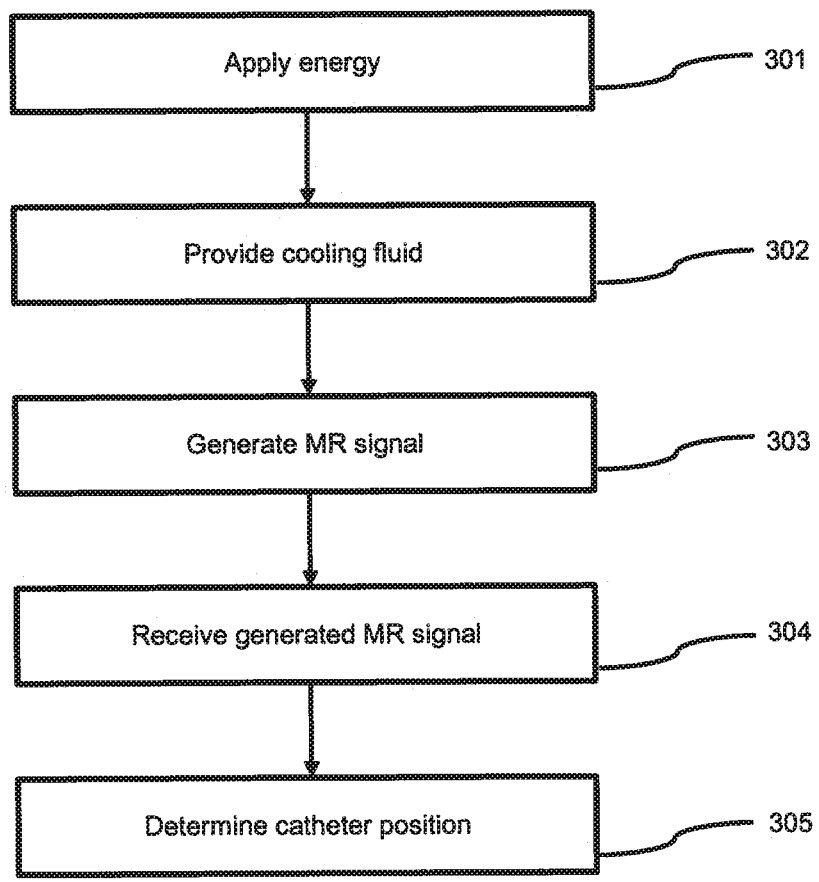
FIG. 6 shows a flow chart exemplarily illustrating an embodiment of a method for localizing a catheter.

In the following a method for applying energy to an object will be exemplarily described with reference to a flowchart shown in FIG. 6.

In step 301, energy is applied to the object by an energy application element of the catheter. As already mentioned above, the energy application element is preferentially an ablation electrode. In step 302, a cooling fluid for cooling the energy application element is provided as magnetic resonance fluid in the cavity of the catheter.

In step 303, a magnetic resonance signal is generated in the magnetic resonance fluid present in the cavity of the catheter such that the generated magnetic resonance signal is receivable by the tracking coil, i.e. in the above described embodiments, a magnetic resonance signal is generated in the magnetic resonance fluid within the most sensitive region of the tracking coil, i.e. within the center of the tracking coil. This generation can be performed by a non-selective excitation of magnetization in a larger volume containing the catheter by the whole body RF coil, wherein the magnetization is read out during a read-out gradient in one spatial dimension, for example, the x-direction by the tracking coil. The receiving of the generated magnetic resonance signal by the tracking coil, in particular, the read out of the magnetization during a read-out gradient in one spatial dimension, for example, the x-direction, is performed in step 304.

In step 305, the catheter position determination unit determines the position of the catheter based on the magnetic resonance signal received by the tracking coil. In particular, the magnetization read out during a read-out gradient in one spatial dimension provides a projection of the signal onto the respective direction, in particular, onto the x-direction. The projection effectively contains a high signal peak corresponding to the x-position or the several x-positions of the tracking coil or of the several tracking coils 15, 115, 215, 315 and noise or low signal received from longitudinal tracking coils 335, if present, elsewhere. Repeated for the two other spatial directions, for example, the y- and the z-direction, the complete position of the respective tracking coil can be determined, in particular, within few ten milliseconds.

It should be noted that step 301 can be performed before, during, or after steps 302 to 305 are performed. Moreover, step 302 can be performed continuously, wherein steps 303 to 305 and steps 301 can be performed automatically or activated by a user at desired times.

Figure 7:
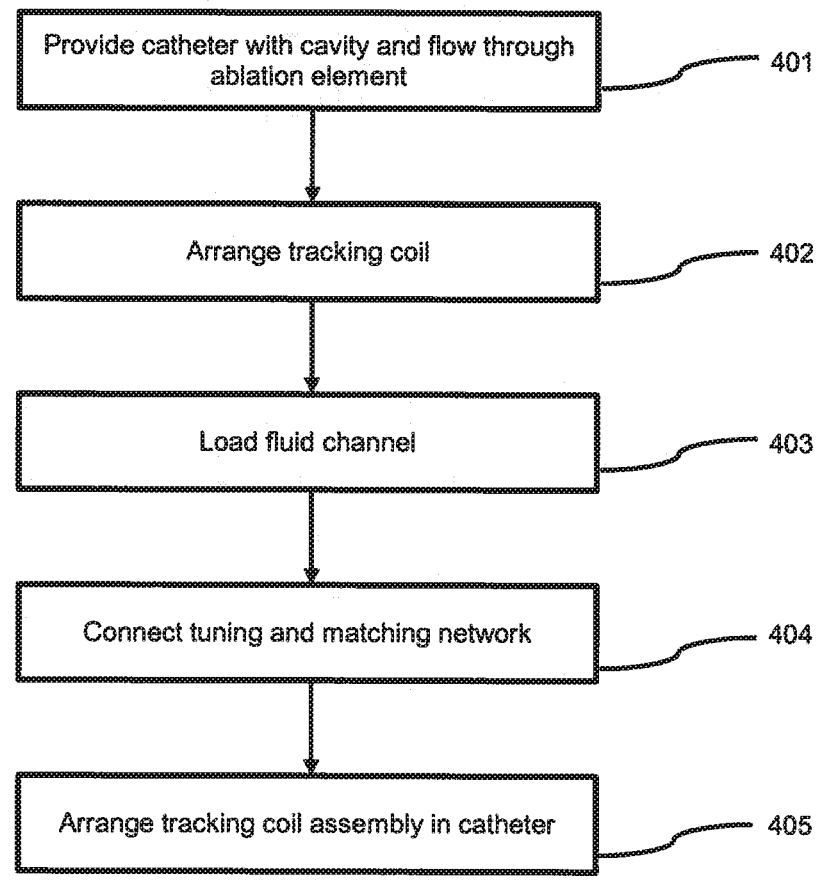
FIG. 7 shows a flow chart exemplarily illustrating an embodiment of a method for manufacturing a catheter.

In the following a method for manufacturing a catheter will be described exemplarily with reference to a flow chart shown in FIG. 7.

In step 401, a catheter, a tracking coil and a cavity formed by a fluid channel, in particular, being a cooling tube, and a feed-through of an ablation element, which is connected to the fluid channel, are provided. Furthermore, a tuning and matching network is provided in step 401.

In step 402, the tracking coil is arranged, preferentially wound, around the fluid channel and the tracking coil is connected to the tuning and matching network, in particular, the tracking coil is solder connected to the tuning and matching network.

In step 403, the fluid channel is loaded with the magnetic resonance fluid being preferentially water saline and the capacitances of the tuning and matching network are adapted for the tracking coil. This is for example accomplished by measurement of the S11 signal at the proximal end of the tuning and matching network with a network analyzer. Capacitances are chosen such that the S11 signal is minimized. The S11 signal preferentially relates to the S11 element of a two-port scattering matrix. The S11 signal is a reflection parameter so that, if the S11 signal is minimized, the reflection of the magnetic resonance signal received by the tracking coil is minimized. Thus, the adaptation of the tuning and matching network for the tracking coil is preferentially performed such that the reflection of the magnetic resonance signal received by the tracking coil while coupling into the connection cable is minimized.

In step 404, the tuning and matching network is connected to a connection cable, and in step 405 the resulting subassembly comprising the tracking coil surrounding the fluid channel with attached ablation element and connected with the connection cable via the tuning and matching network with the adapted capacitances is arranged within the catheter, in particular, pulled into a lumen of the catheter which can be regarded as a main tube. At completion of step 405 the ablation element is located at the distal end of the catheter and the fluid channel with tracking coil, tuning and matching network, and connection cable are located inside the main tube of the catheter.

The tracking coil is preferentially tuned and matched to the connection cable by using the tuning and matching network like performed with any conventional magnetic resonance receive coil for optimal signal reception. This is preferentially achieved by the tuning and matching network comprising capacitors. The simplest network consists of one capacitor in series and one capacitor in parallel to the tracking coil. The capacitances must be adapted for tuning and matching of the tracking coil and depend sensitively on the impedance of the coil. Since the tracking coils can only be manufactured with some tolerances in impedance which also is influenced by the coil loading, the capacitances are adapted for the tracking coil in the loaded condition.

The magnetic resonance fluid is preferentially adapted to avoid overheating and charring of tissue next to the catheter tip, to avoid blood coagulation, and in return to allow for more radio frequency power for deeper and faster ablation without those effects.

The catheter is preferentially an ablation catheter, wherein a tracking coil is located inside the catheter and wherein the tracking coil uses cooling fluid, in particular, cooling liquid, as signal source. The tracking coil is preferentially arranged at the tip of the catheter. However, the tracking coil can be located at any other part of the catheter whose position has to be determined.

The catheter is preferentially used in electrophysiological interventions, wherein the catheter overcomes several important drawbacks of tip coil setups applied so far to magnetic resonance electrophysiological catheters. Firstly, they suffer from an "empty" tip coil without water in its core and hence a sub-optimal localization signal. Secondly, their tip coil is mounted on the outside of the main tube. This adds to the catheter profile, and for a connection of a cable inside the tube a hole must be cut into the tube which weakens its mechanics and is a potential leak for blood. This means the catheter in accordance with the invention provides an improved radio frequency safety and biocompatibility. In particular, the tracking coil is provided with a cooling fluid being preferentially a cooling liquid as signal source in its most sensitive region yielding an optimal magnetic resonance signal. Furthermore, preferentially the internal tracking coil does not add to the catheter profile, and the internal tracking does not require feedthrough of a coil wire from outside to inside. The main tube, i.e. the outer tube, of the catheter stays preferentially completely intact and weak spots are avoided. The assembly of the catheter becomes much simpler. The tip coil can be premounted to a cooling tube, it can be electrically loaded by filling the tubes and then the capacitances of the tuning and matching network can be adapted, and the resulting subassembly can be inserted into a main tube.

The catheter can be designed as a catheter for open tip irrigation or as closed loop system. In both designs, cold saline is preferentially used to cool the catheter tip during radio frequency delivery.

In an open tip irrigation system cold saline is pumped through the fluid channel being an internal tube along the catheter, in particular, along the shaft of the catheter, and is forced out of openings in a porous catheter tip. Thus, although in the embodiment described above with reference to FIG. 4 a single opening is used for irrigation, alternatively also a porous catheter tip comprising several openings can be used for irrigation. The saline eventually empties into the blood pool.

In the closed loop system cold saline is similarly pumped to the catheter tip but via a second tube, or via the same tube after a bend of 180°, returns back to the pump which might be located inside or outside the catheter. The cooled catheter may result in fewer impedance rises, a decrease in coagulum risk, an ability to lengthen radio frequency application times, and an achievement of larger lesion size.

The catheter and the magnetic imaging system are preferentially adapted for localizing the tracking coil during an ablation procedure. The tracking coil is preferentially an active tracking coil being a magnetic resonance receive coil, in particular, being a miniature magnetic resonance receive coil.

The connection cable for connecting the tracking coil which is arranged within the catheter is preferentially a transformer-based cable to avoid unwanted radio frequency heating of the catheter by the magnetic resonance imaging system as, for example, described in "Transmission Line for Improved RF Safety of Interventional Devices", Weiss S, Vernickel P, Schaeffter T, Schulz V, Gleich B, Magn Reson Med 2005; 54, 182-189. The widening within the tracking coil as, for example, described above with reference to FIG. 3, is preferentially dimensioned such that the tracking coil is completely filled for generating a large magnetic resonance signal.

Preferentially, a magnetic resonance contrast agent is mixed into the magnetic resonance fluid being preferentially a cooling liquid to increase the tracking signal. The contrast concentration is optimized for the purpose of tracking. During cooling, the inflow of the magnetic resonance fluid into the coil provides fresh spins which further increases the tracking signal. As a positive side effect, the full length catheter may be visualized in magnetic resonance images by means of the fluid channel comprising the magnetic resonance fluid, in particular, by means of cooling tubes comprising a cooling liquid as magnetic resonance fluid.

The dosage of the a magnetic resonance contrast agent mixed into the magnetic resonance fluid is preferably the dosage as for use of the agent for standard contrast enhanced magnetic resonance imaging. For example, using For Magnevist (bottle concentration 469.01 mg/ml), concentrations between 0.2 mL of bottle fluid per kg of magnetic resonance fluid and 0.6 mL of bottle fluid per kg of magnetic resonance fluid may be used.

Although in the above described embodiments, only a single tracking coil is shown, the catheter can also comprise more than one tracking coil, in particular, for localizing several parts of the catheter. Furthermore, a tracking coil can also be arranged at another part of the catheter not being the catheter tip.

Although in the above described embodiments different configurations of a tracking coil and a cavity for providing a magnetic resonance fluid are shown, the catheter can comprise any arrangement of tracking coil and cavity for providing a magnetic resonance fluid which allows providing a magnetic resonance fluid being a cooling fluid for cooling the energy application element, from which magnetic resonance signals are receivable, wherein the tracking coil is adapted for receiving the magnetic resonance signals from the magnetic resonance fluid. In particular, the catheter can comprise any arrangement of tracking coil and cavity for providing the magnetic resonance fluid being a cooling fluid, wherein the cavity is the fluid channel and wherein the tracking coil surrounds the fluid channel.

In particular, also the distal ends shown in FIGS. 3 to 5 can comprise ring electrodes 40, 41 and/or a further short solenoidal coil. Furthermore, also the distal ends of the catheters shown in FIGS. 2 to 4 can comprise an elongated tracking coil as, for example, shown in FIG. 5. Thus, the different elements shown in FIGS. 2 to 5 can be combined to a desired catheter.

Although in the above described embodiments each tracking coil is separately connected to a tuning and matching network, wherein each tuning and matching network is separately connected to the magnetic resonance receiver, in another embodiment several tracking coils can be connected to the same tuning and matching network. In this case, during determining the position of the respective tracking coil the projection of the signal onto, for example, the x-direction contains several signal peaks at specific locations corresponding to the several tracking coils, wherein these specific locations correspond to, for example, the x-coordinates of the tracking coils.

The catheter control unit can be adapted to control the application of energy via an ablation element for performing an ablation procedure. Furthermore, the catheter control unit can be adapted to control a recording and/or pacing procedure, and the catheter control unit can be adapted to control the flow of the magnetic resonance fluid through the cavity being preferentially a fluid channel. The catheter control unit can be comprised of several units fulfilling these functions.

The catheter is preferentially a catheter adapted for an interventional ablation procedure within a heart of a person. However, the catheter can also be adapted for performing another procedure, for example, in another object like another organ of a person or like a technical object. For example, the catheter can be used for applying energy like light energy or electrical energy within a technical object, wherein the position of the catheter is determined by using the magnetic resonance imaging system, the magnetic resonance fluid in the cavity and the tracking coil of the catheter.

It should be noted that all catheters, in particular, all distal ends of catheters, described above can be used together with the further components shown in FIG. 1.

The catheter comprising the energy application element, the cavity and the tracking coil can be adapted such that the cavity is suitable for providing a magnetic resonance fluid being a cooling fluid only or being a cooling fluid which can also be used for other purposes like irrigation purposes.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to a catheter for applying energy to an object and a magnetic resonance imaging system for localizing the catheter. The catheter comprises an energy application element for applying energy to the object, and a cavity for providing a magnetic resonance fluid from which magnetic resonance signals generated by the magnetic resonance imaging system are receivable, wherein the cavity is adapted for providing a cooling fluid as the magnetic resonance fluid for cooling the energy application element. The catheter comprises further a tracking coil for tracking the catheter, wherein the tracking coil is adapted to receive the magnetic resonance signals from the magnetic resonance fluid. Thus, the magnetic resonance fluid fulfils at least two functions, providing magnetic resonance signals for tracking the catheter and cooling the energy application element.

The invention claimed is:

1. A catheter for applying energy to an object being usable in a magnetic resonance imaging system, the catheter comprising:

an energy application element for applying energy to an object, a cavity for providing a magnetic resonance fluid from which magnetic resonance signals are receivable, wherein the cavity is configured to provide a channel guiding a flow of the magnetic resonance fluid through the catheter to the energy application element as a cooling fluid for cooling the energy application element, a tracking coil for tracking the catheter, the tracking coil being an active magnetic resonance receive coil configured to receive the magnetic resonance signals from the magnetic resonance fluid, wherein the tracking coil surrounds the cavity.

2. The catheter of claim 1, wherein the cavity and the tracking coil are inside of the catheter.

3. The catheter of claim 1, wherein the magnetic resonance fluid comprises a magnetic resonance contrast agent, the cavity is configured to allow the magnetic resonance fluid to leave the catheter at a distal end of the catheter, and the magnetic resonance fluid leaving the catheter marks ablated tissue.

4. The catheter of claim 1, wherein the catheter comprises a flexible distal tip and the magnetic resonance fluid comprises a magnetic resonance contrast agent which enhances visibility of the flexible distal tip of the catheter in a magnetic resonance image.

5. A system for ablating tissue, comprising:
a magnetic resonance system;
a catheter, comprising:
an energy application element for applying energy to an object at a distal end of the catheter;
a cavity for providing a magnetic resonance fluid from which magnetic resonance signals are receivable, wherein the cavity is configured to provide a channel guiding a flow of the magnetic resonance fluid through the catheter to the energy application element as a cooling fluid for cooling the energy application element; and
a tracking coil for tracking the catheter, the tracking coil being an active magnetic resonance receive coil configured to receive the magnetic resonance signals from the magnetic resonance fluid, wherein the tracking coil surrounds the cavity; and
a processor configured to determine a position of the tracking coil based on the received magnetic resonance signals.

6. A method of ablating tissue of a patient in a magnetic resonance system, comprising the steps of:
controlling an energy application element at a distal tip of a catheter to apply energy to the tissue;
providing a flow of magnetic resonance fluid to the energy application element through a channel within the catheter;
exciting magnetic resonance in the flow of magnetic resonance fluid;
receiving magnetic resonance signals from the magnetic resonance fluid at an active magnetic resonance receive coil surrounding the channel; and
determining a location of the active magnetic resonance receive coil based on the received magnetic resonance signals.

* * * * *